US012765696B2

(12) United States Patent
Peng

(10) Patent No.: US 12,765,696 B2
(45) Date of Patent: Oct. 20, 2026

(54) INTELLIGENT BED MATTRESS

(71) Applicant: TMAXSTRATEGY & MARKETING INC., New Taipei City (TW)

(72) Inventor: Hong Grong Peng, New Taipei City (TW)

( * ) Notice: Subject to any disclaimer, the term of this patent is extended or adjusted under 35 U.S.C. 154(b) by 28 days.

(21) Appl. No.: 18/890,004

(22) Filed: Sep. 19, 2024

(65) Prior Publication Data

US 2025/0235010 A1 Jul. 24, 2025

(51) Int. Cl.

*A47C 31/12* (2006.01)
*A47C 17/86* (2006.01)
*A61B 5/024* (2006.01)

(52) U.S. Cl.

CPC ............ *A47C 31/123* (2013.01); *A47C 17/86* (2013.01); *A61B 5/024* (2013.01)

(58) Field of Classification Search

CPC ....... A47C 17/16; A47C 17/86; A47C 27/006; A47C 31/008; A47C 31/123; A61B 5/6892; A61B 5/0507; A61B 5/024
See application file for complete search history.

(56) References Cited

U.S. PATENT DOCUMENTS

| | | | | |
|---|---|---|---|---|
| 2019/0159695 | A1* | 5/2019 | Kogure | A61B 5/0205 |
| 2020/0405998 | A1* | 12/2020 | Franceschetti | G16H 40/63 |
| 2021/0204720 | A1* | 7/2021 | Karschnik | A47C 21/044 |
| 2022/0087534 | A1* | 3/2022 | Mansky | A61B 5/01 |

FOREIGN PATENT DOCUMENTS

| | | | | | |
|---|---|---|---|---|---|
| CN | 106943258 | A | * | 7/2017 | A61M 21/02 |
| CN | 209769785 | U | * | 12/2019 | |
| CN | 107072565 | B | * | 7/2020 | A61B 5/369 |
| DE | 102021208524 | A1 | * | 3/2022 | G01K 13/20 |
| DE | 102025100623 | A1 | * | 7/2025 | A47C 27/006 |
| JP | 2006263454 | A | * | 10/2006 | |
| JP | 2016198121 | A | * | 12/2016 | B60N 2/0029 |
| JP | 2017047078 | A | * | 3/2017 | |
| JP | 2021178198 | A | * | 11/2021 | A61B 5/6892 |
| JP | 2023549729 | A | * | 11/2023 | G01L 1/20 |
| KR | 20200139023 | A | * | 12/2020 | A61B 5/0002 |
| WO | WO-2015046055 | A1 | * | 4/2015 | B60N 2/0029 |
| WO | WO-2019143953 | A1 | * | 7/2019 | A61B 5/6892 |
| WO | WO-2021138527 | A2 | * | 7/2021 | G05B 19/4155 |

* cited by examiner

*Primary Examiner* — David E Sosnowski
(74) *Attorney, Agent, or Firm* — Alexander Chen

(57) ABSTRACT

The present invention provides an intelligent bed mattress, which mainly uses a non-contact sensor to detect the physiological information of the human body. Through remote life information detection, it acquires the life information of the user by tracking the REM (rapid eye movement), monitoring the heartbeat, and detecting the breathing, and also captures and records the physiological information of the user by detecting time of leaving the bed and sleeping position. Through a control box, it can be connected with a mobile device or computer via Bluetooth pairing, and all of the captured information can be displayed or uploaded to a cloud database for storage. In this way, it can provide long-term measuring or real-time monitoring of the physiological information of the user, to facilitate the establishment of an accurate care modal.

7 Claims, 6 Drawing Sheets

INTELLIGENT BED MATTRESS

INCORPORATION BY REFERENCE

This application claims the benefit of priority under 35 U.S.C. 119 to the filing date of the Taiwan patent application No. 113102796, entitled "INTELLIGENT BED MATTRESS," which was filed on Jan. 24, 2024, and which is incorporated herein by reference in its entirety.

BACKGROUND OF INVENTION

1. Field of the Invention

The present invention relates generally to a bed mattress, and more particularly to an intelligent bed mattress having a non-wearing and non-contact sensor to detect various vital signs of the human body.

2. Description of Related Art

The intelligent bed mattresses sold on the current market can measure and capture various users' life information in need, by using a variety of contact or non-contact physiological measuring techniques. Human vital information can be very useful in related fields in the future. The intelligent bed mattresses also provide soft pressure detection to obtain the movement or position of the user's body to determine the quality of sleep and also to alert the risk of falling from the bed or the frequency of leaving beds at night. Such information can help establish a plan for healthy sleep and be used for sleep management.

For example, the feature of heart rate and breath rate can indicate a lot of information. The most obvious is sign of life. Mostly, the status of sleep is analyzed by use of brain wave. However, detecting brain wave, the user is going to have to wear tangible wires, patches or other devices, which may affect the sleep quality of the user. If the analysis can be conducted using heart rate as well as breath rate, this problem can be avoided. The information of heart can indicate the status of sleep, and be used to judge the degree of fatigue of the user. It can even be used to detect sleep apnea. In the modern days, people are increasing aware of healthcare and are paying more attention to health and exercise. The information of heart rate and breath rate can be used to evaluate the effectiveness of exercise. Using movement sensors, pedometers are developed to record the state of exercise. The change of heart rate is also related to the status of sympathetic nerves and parasympathetic nerves, whereas the activeness of sympathetic nerves and parasympathetic nerves is in connection with emotion. Therefore, by analyzing heart rate can, we can have a preliminary understanding of the emotional state.

Current techniques for the detection of various physiological data during sleep of the user include: Ultra Wide Band (UWB), Force-Sensitive Resistor, Optical Fiber Sensing, Capacitor Conduction Sensing etc. However, the above existing techniques are either unable to accurately judge the position of the user, or too costly, and are therefore not suitable for home use or mobile use. In addition, the general wearable devices such as Apple iWatch must be tightly attached to the skin of the wrist to avoid interference of environmental noises. Otherwise, inaccurate measurement may mislead the judgement.

Hence, it is a goal for researchers and developers to find solutions to measure life information and various physiological information of the human body in a simple and accurate way.

SUMMARY OF THE INVENTION

The object of the present invention is to provide an intelligent bed mattress to solve the problems that the existing techniques for measuring physiological data of the human body must require direct contact, or real-time monitoring, or long-term monitoring. The present invention adopts a non-contact "nanosecond pulse near-field radar detection" technique. The micro radar used in this technique is capable of detection through the clothing, not affected by the wearing form or environmental interferences. A non-wearing physiological detection device based on the present invention can provide more comfort and higher accuracy of collecting life information, and will certainly better meet the requirement of average consumers.

Another object of the present invention is to provide an intelligent bed mattress having penetrability and is capable of detection through obstacles like clothing, bedding, and protective gear, thus effectively reducing the interference from the environment.

To accomplish the above objects, the inventor of the present invention has developed an intelligent bed mattress, comprising: a surface structure; a lining structure, embedded inside the surface structure, the lining structure further comprising: a bottom layer, to provide elastic support; a middle layer, bonded with and covering the surface of the bottom layer, and deployed with a soft and flexible radar antenna to detect and record the life information of the user, more than one force-sensitive resistor, to detect and record the physiological information of the user, and a set of first electric connection points, respectively connected to the soft and flexible radar antenna and the force-sensitive resistors for electric conduction; a top layer, bonded with and covering the surface of the middle layer, and configured with a set of second electric connection points at positions corresponding to the set of first electric connection points; and a control box, a printed circuit board is provided inside as the main control unit, comprising a power supply circuit and a Bluetooth module, the bottom of the control box is configured with a set of third electric connection points in a convex form, which can coincide and be electrically connected with the second electric connection points, one side of the control box a is configured with a clamshell, having an electric socket inside.

In one embodiment, the surface structure is a waterproof but breathable fabric sleeve with three sides sealed and one side open.

In one embodiment, the bottom layer is a soft cushion made of PU material.

In one embodiment, the middle layer is made of transparent or semitransparent plastic material.

In one embodiment, the top layer is a thin cotton soft cushion.

In one embodiment, the power source of the power supply circuit is commercial electricity connected via an electric socket or battery fitted inside the control box.

In one embodiment, the control box is connected to a mobile device or computer via Bluetooth pairing.

DETAILED DESCRIPTION OF THE INVENTION

Figure 1:
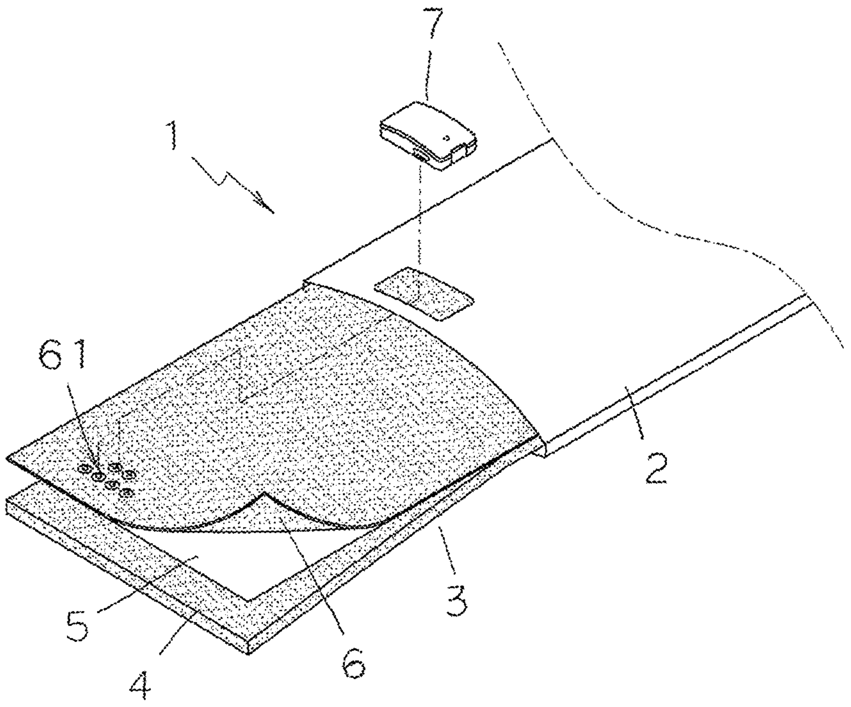
FIG. 1 is an exploded structural view of the intelligent bed mattress according to a preferred embodiment of the present invention.

Referring collectively to FIG. 1~FIG. 4, the present invention provides an intelligent bed mattress (1), mainly comprising: a surface structure (2), which, in the present embodiment, adopts a medical class waterproof but breathable fabric sleeve, having antimicrobial, mildew-proof, skin-friendly, stain-resistant and flame-retardant effects, and the surface structure (2) is a fabric sleeve with three sides sealed and one side open; a lining structure (3), embedded inside and covered by the fabric sleeve of the surface structure (2), the lining structure (3) further comprising: a bottom layer (4), which can be a soft cushion made of any material, but made of PU material in the present embodiment for good elastic support to avoid excessive pressure in some areas of the body; a middle layer (5), bonded with and covering the surface of the bottom layer (4), made of transparent or semitransparent plastic material, the surface of the middle layer (5) being deployed with: a soft and flexible radar antenna (51) to detect and record the physiological information of the user, more than one force-sensitive resistor (52) to sense and record the physiological information of the user, such as information of leaving the bed and position of sleep etc., and a set of first electric connection points (53), respectively connected with the soft and flexible radar antenna (51) and the force-sensitive resistors (52) for electric conduction; a top layer (6), bonded with and covering the surface of the entire middle layer (5) to protect the structure of the middle layer (5), being a thin cotton soft cushion in the present embodiment, furthermore, the top layer (6) is configured with a set of second electric connection points (61) at positions corresponding to the first electric connection points (53) for electric connection; and a control box (7), configured with a printed circuit board inside as the main control unit, comprising a power supply circuit, with commercial electricity or battery provided as its power source; a Bluetooth module, provided for wireless communication, which can be paired and connected with any mobile device or remote computer, the bottom surface of the control box (7) is configured with a set of third electric connection points (71) in a convex form, which can completely coincide with the second electric connection points (61) and the first electric connection points (53) for electric conduction, one side of the control box (7) is provided with a clamshell (72), having an electric socket (73) inside for connection to commercial electricity via wires. Moreover, the control box (7) can be designed in a detachable form for independent cleaning and maintenance.

Figure 2:
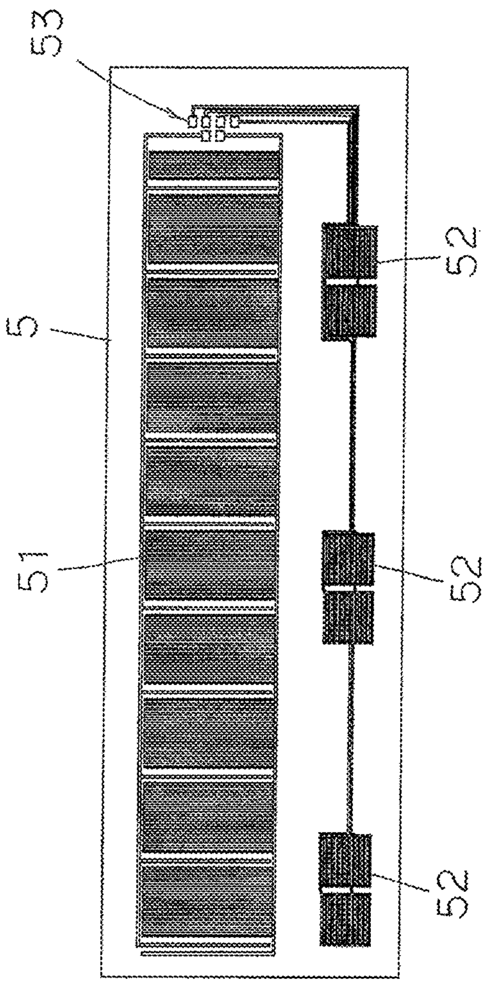
FIG. 2 is a structural view of the middle layer of the intelligent bed mattress according to a preferred embodiment of the present invention.

Referring to FIG. 2, the soft and flexible radar antenna (51) of the present invention is deployed and embedded inside the middle layer (5), and is electrically connected to the first electric connection points (53). Featuring non-contact detection, a 300~500 MHz near-field radar can sense the life information from a distance of 15 cm and has the following functions: 1, tracking the rapid eye movement of the user, sleeping state of the user, such as light sleep, deep sleep, or awake; 2, monitoring the heartbeat of the user and alerting fatal arrhythmia or auricular fibrillation; 3, sensing the breathing of the user and alerting sleep apnea; the multiple sets of force-sensitive resistors (52) are also configured inside the structure of the middle layer (5) and are also electrically connected to the set of first electric connection points (53), having the following functions: detecting bed-leaving information of the user, so as to analyze and track sleepwalking, polyuria, and three-stage bed-leaving alerts (sitting-up, bed-edge, leaving), to remind bed-leaving in time to effectively avoid fall, and also to prevent pressure ulcer by monitoring bad sleep position and toss and turn.

The above first electric connection points (53) and corresponding second electric connection points (61) are respectively configured in the lining structures (3) of different layers, and coincide with each other for electric conduction. The control box (7) is positioned above to cover the set of second electric connection points (61). The corresponding third electric connection points (71) on the bottom surface of the control box (7) are electrically connected with the second electric connection points (61) and the first electric connection points (53). The detected life information and sensed physiological information are transmitted to the control box (7). A built-in Bluetooth module provides wireless communication through pairing and connection with a mobile device or remote computer, so that the above information can be sent to the mobile device or remote computer and be displayed. The information can also be uploaded to a cloud database for storage.

Figure 3A:
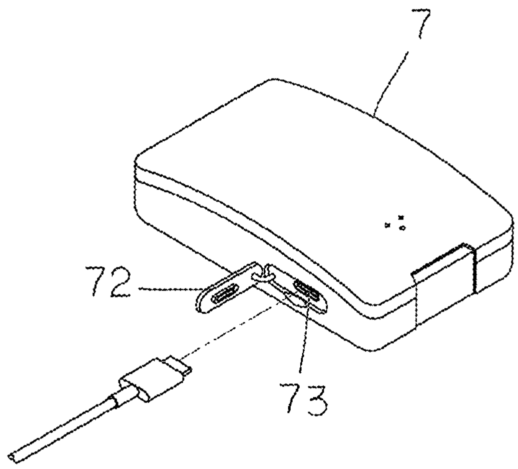
FIG. 3(A) and FIG. 3(B) are structural views from different angles of the control box of the intelligent bed mattress according to a preferred embodiment of the present invention.
Figure 3B:
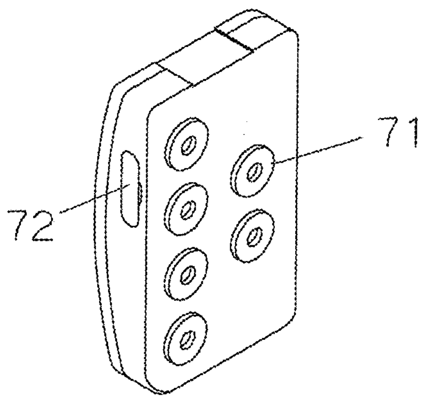
Figure 4:
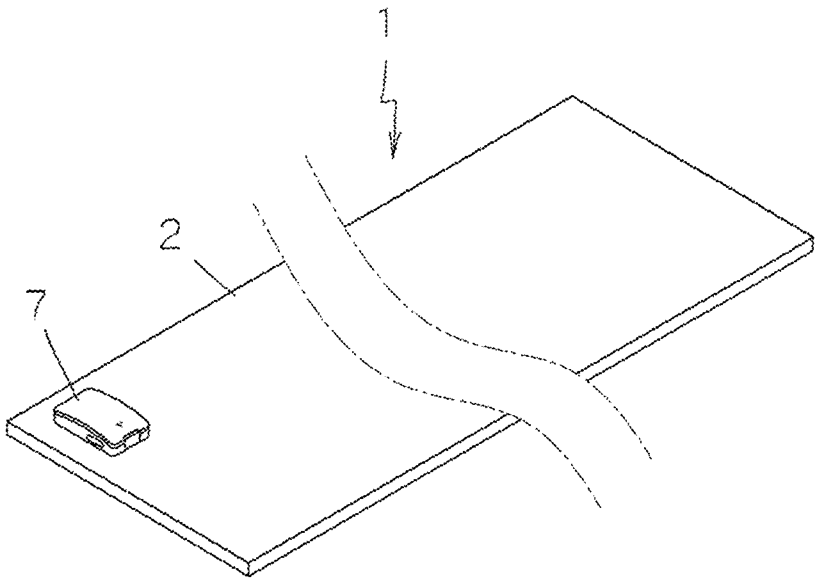
FIG. 4 is perspective view of the intelligent bed mattress according to a preferred embodiment of the present invention.

Referring to FIG. 3(A) and FIG. 3(B), the control box (7) of the present invention is the power source to supply electricity for the operation of the entire intelligent bed mattress. There is an electric socket (73) inside the clamshell (72) on one side of the control box (7), which can be connected to commercial electricity through wires. Meanwhile, the control box (7) is also fitted with batteries to maintain normal operation for 36 hours in case the commercial electricity is cut off. Therefore, accidental blackout is no worry.

Figure 5:
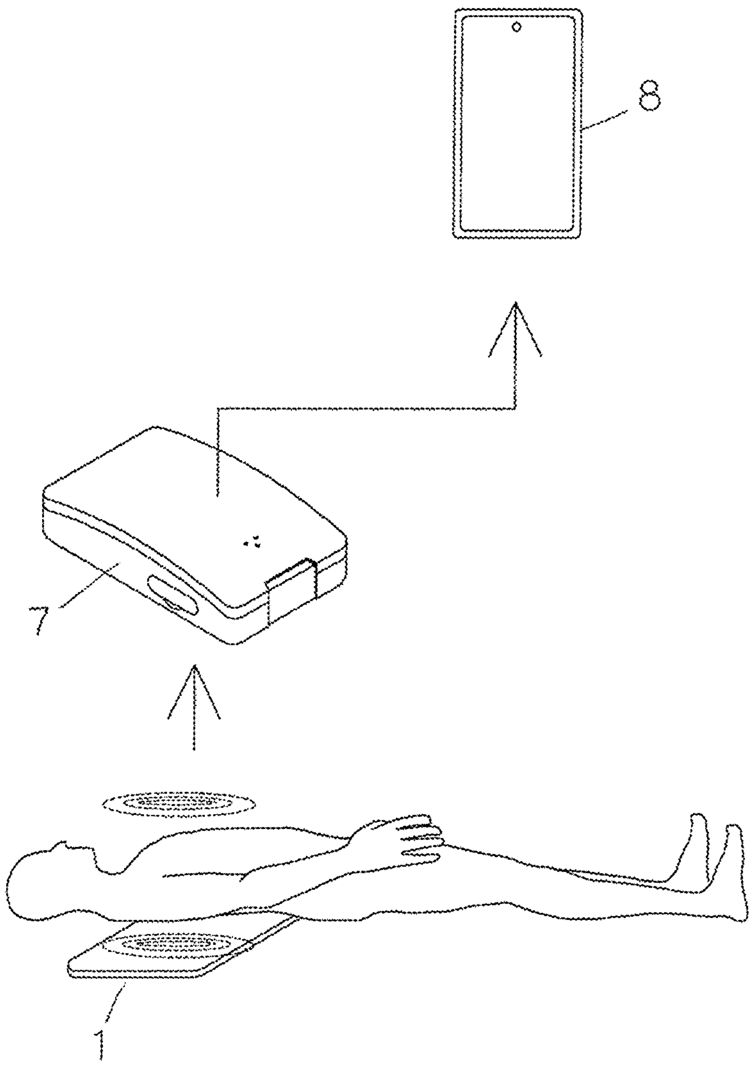
FIG. 5 is an implementation view (I) of the intelligent bed mattress according to a preferred embodiment of the present invention.
Figure 6:
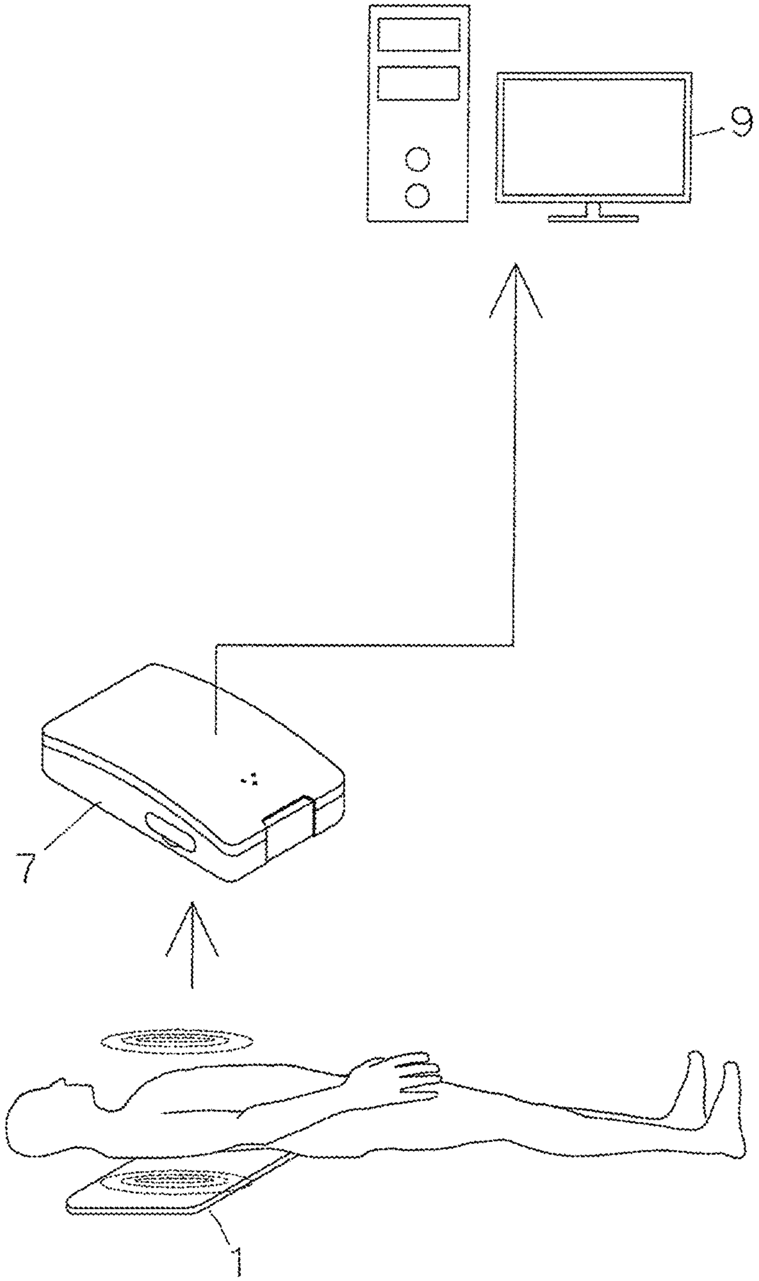
FIG. 6 is an implementation view (II) of the intelligent bed mattress according to a preferred embodiment of the present invention.

Referring to the embodiments (I)(II) shown in FIG. 5 and FIG. 6, when using the intelligent bed mattress of the present invention, the intelligent bed mattress (1) is put below the pillow in the bed (approximately the position of the chest), when commercial electricity is connected to the control box (7) via wires, the intelligent bed mattress (1) is started to work, without the need to operate a switch; when the user lies on the intelligent bed mattress (1), the flexible radar antenna (51) will detect the pulse of the user, the time interval between sending and returning the pulse signal will vary, and this variation is transformed to life information such as breathing and heartbeat, and transmitted to the control box (7). Then, via Bluetooth, the information is sent to the paired mobile device (8) or computer (9). Such life information can be further uploaded to a cloud database for storage and subsequent tracking. Meanwhile, the force-sensitive resistor (52) will simultaneously detect the bed-leaving information of the user, include three-stage bed-leaving reminding (sitting-up, bed-edge, bed-leaving), so as to timely remind bed-leaving to prevent fall. It also monitors the sleeping position and situation of toss and turn for effective prevention of pressure ulcer; Similarly, the sensed information can be transmitted to and displayed on the paired mobile device (8) or computer (9) via the control box (7) and Bluetooth, or be uploaded to a cloud database for storage. Then, such information can be used for analysis and tracking, to judge if the user has cases of sleepwalking, polyuria etc.

The intelligent bed mattress designed by the present invention has the following added values: (1) Catering to insomniacs and old solitary people, reducing burden of medical care personnel, and avoiding the necessity of wearable detecting devices that may affect health. (2) Convenient installation and operation, the intelligent bed mattress can be placed under the front chest and be started simply by connecting it to electric power source. (3) Life information detected by flexible and non-contact sensors can be used to interpret the sleep condition, heart beat and breathing of the user, so as to judge if the user has diseases of arrhythmia (auricular fibrillation) or sleep apnea. (4) The physiological information detected by the force-sensitive resistor can be used to interpret bed-leaving information for analysis and tracking of sleepwalking or polyuria to prevent fall, and be used to monitor the sleeping position and situation of toss and turn to prevent pressure ulcer, or to record snores and night coughs. (5) Pairing with a mobile device to record all life and physiological information of the user. (6) In case of accidental blackout, the batteries can supply electricity to maintain normal operation for 36 hours. (7) When at home, a hospital or a nursing home, doctors and nurses can monitor the information of the patient in a remote and real-time manner. (8) The control box is in a detachable design for convenient cleaning and maintenance. (9) All information can be stored in a cloud database.

Although the invention has been explained in relation to its preferred embodiment, it is to be understood that many other possible modifications and variations can be made without departing from the spirit and scope of the invention as hereinafter claimed.

The invention claimed is:

1. An intelligent bed mattress, comprising:

a surface structure;

a lining structure embedded inside the surface structure, the lining structure comprising:

a bottom layer configured to elastically support a user;

a middle layer bonded to and covering a surface of the bottom layer, the middle layer comprising:

a radar antenna configured to sense breathing information and heartbeat information of the user and generate a first signal corresponding to the sensed breathing information and heartbeat information;

a plurality of force-sensitive resistors configured to sense pressure changes corresponding to bed-leaving information, sleeping position information, and toss-and-turn status of the user and generate a second signal corresponding to the sensed pressure changes; and a set of first electrical connection points electrically connected to the radar antenna and the plurality of force-sensitive resistors;

a top layer bonded to and covering a surface of the middle layer, the top layer comprising a set of second electrical connection points positioned to correspond to the set of first electrical connection points; and a control box comprising:

a printed circuit board including a main control unit, a power supply circuit, and a Bluetooth module;

a set of third electrical connection points disposed on a bottom surface of the control box and configured to electrically connect with the set of second electrical connection points;

a clamshell disposed on one side of the control box; and an electric socket disposed inside the clamshell, wherein the main control unit is configured to process the first signal to determine breathing information and heartbeat information of the user and to process the second signal to determine at least one of bed-leaving information, sleeping position information, and toss-and-turn status of the user.

2. The intelligent bed mattress defined in claim 1, wherein said surface structure is a waterproof but breathable fabric sleeve with three sides sealed and one side open.

3. The intelligent bed mattress defined in claim 1, wherein said bottom layer is a polyurethane cushion layer.

4. The intelligent bed mattress defined in claim 1, wherein said middle layer is made of transparent or semi-transparent plastic material.

5. The intelligent bed mattress defined in claim 1, wherein said top layer is a cotton cushion layer.

6. The intelligent bed mattress defined in claim 1, wherein the power source of said power supply circuit is commercial electricity connected via an electric socket or battery fitted inside the control box.

7. The intelligent bed mattress defined in claim 1, wherein said control box Bluetooth module is configured to wirelessly communicate with a mobile device or a computer via Bluetooth pairing.

* * * * *